US012766193B2

(12) United States Patent
Zhang et al.

(10) Patent No.: US 12,766,193 B2
(45) **Date of Patent: *Oct. 20, 2026**

(54) ANTI-CD133 SINGLE-CHAIN ANTIBODY AND USE THEREOF IN PREPARATION OF DRUG FOR TREATING TUMOR

(71) Applicant: Beijing Neurosurgical Institute, Beijing (CN)

(72) Inventors: Wei Zhang, Beijing (CN); Tao Jiang, Beijing (CN); You Zhai, Beijing (CN); Guanzhang Li, Beijing (CN)

(73) Assignee: Beijing Neurosurgical Institute, Beijing (CN)

( * ) Notice: Subject to any disclaimer, the term of this patent is extended or adjusted under 35 U.S.C. 154(b) by 726 days.

This patent is subject to a terminal disclaimer.

(21) Appl. No.: 18/018,778

(22) PCT Filed: Jul. 30, 2021

(86) PCT No.: PCT/CN2021/109863

§ 371 (c)(1),
(2) Date: Jan. 30, 2023

(87) PCT Pub. No.: WO2022/022718

PCT Pub. Date: Feb. 3, 2022

(65) Prior Publication Data

US 2023/0310603 A1 Oct. 5, 2023

(30) Foreign Application Priority Data

Jul. 31, 2020 (CN) ......................... 202010762998.4

(51) Int. Cl.

| | |
|---|---|
| ***C07K 16/28*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/705*** | (2006.01) |
| ***C07K 14/715*** | (2006.01) |
| ***C12N 5/0783*** | (2010.01) |
| ***C12N 15/86*** | (2006.01) |

(52) U.S. Cl.

CPC .............. *A61K 40/31* (2025.01); *A61K 40/11* (2025.01); *A61K 40/4204* (2025.01); *A61K 40/4224* (2025.01); *A61P 35/00* (2018.01); *C07K 14/7155* (2013.01); *C07K 16/2803* (2013.01); *C07K 16/2896* (2013.01); *C12N 5/0636* (2013.01); *C12N 15/86* (2013.01); *A61K 2239/47* (2023.05); *C07K 2319/02* (2013.01); *C07K 2319/03* (2013.01); *C12N 2501/2302* (2013.01); *C12N 2740/15043* (2013.01)

(58) Field of Classification Search

None

See application file for complete search history.

(56) References Cited

U.S. PATENT DOCUMENTS

| | | | | |
|---|---|---|---|---|
| 8,722,858 B2 | 5/2014 | Yoshida | | |
| 2010/0209439 A1 | 8/2010 | Yoshida | | |
| 2019/0330362 A1 | 10/2019 | Moffat et al. | | |
| 2020/0157227 A1 | 5/2020 | Chang et al. | | |
| 2023/0295294 A1* | 9/2023 | Zhang | C12N 7/00 | 424/93.21 |
| 2023/0322940 A1* | 10/2023 | Zhang | C07K 16/2884 | 424/134.1 |
| 2024/0052014 A1* | 2/2024 | Zhang | A61K 40/4202 | |

FOREIGN PATENT DOCUMENTS

| | | |
|---|---|---|
| CN | 109735500 A | 5/2019 |
| CN | 110526970 A | 12/2019 |
| CN | 110526987 A | 12/2019 |
| CN | 111278455 A | 6/2020 |
| EP | 2 175 016 A1 | 4/2010 |

OTHER PUBLICATIONS

Extended European Search Report with Supplementary European Search Report and the European Search Opinion, issued by the European Patent Office for corresponding European Patent Application No. 21849059.7, dated Jun. 24, 2024.

International Search Report and Written Opinion of the International Searching Authority issued by the China National Intellectual Property Administration for International Patent Application No. PCT/CN2021/109863, mailed on Sep. 28, 2021, with an English translation.

* cited by examiner

*Primary Examiner* — Ilia I Ouspenski

(74) *Attorney, Agent, or Firm* — MYERS WOLIN, LLC

(57) ABSTRACT

The disclosure relates to an anti-CD133 single-chain antibody. The amino acid sequence of the anti-CD133 single-chain antibody comprises a sequence shown in SEQ ID NO. 1. T lymphocytes expressing the anti-CD133 single-chain antibody can specifically kill CD133-positive tumor cells and have higher specificity and stronger killing ability.

16 Claims, 3 Drawing Sheets

Specification includes a Sequence Listing.

ANTI-CD133 SINGLE-CHAIN ANTIBODY AND USE THEREOF IN PREPARATION OF DRUG FOR TREATING TUMOR

CROSS-REFERENCE TO RELATED APPLICATION

This application is a national stage application under 35 U.S.C. 371 of International Application No. PCT/CN2021/109863, filed on Jul. 30, 2021, which claims priority to Chinese Patent Application No. 202010762998.4, filed on Jul. 31, 2020, the entire contents of each are herein wholly incorporated by reference.

TECHNICAL FIELD

The disclosure relates to the field of pharmaceutical biotechnology, in particular to a chimeric antigen receptor targeting CD133, an encoding nucleic acid, an expression vector, a cell, a pharmaceutical composition and use thereof.

BACKGROUND

Chimeric antigen receptor (CAR) is a synthetic T cell receptor consisting of an antigen binding domain, a transmembrane domain and an intracellular signaling domain. The antigen binding domain is located outside a T cell membrane, includes a single-chain antibody or ligand, and is used for specifically binding to a target antigen. The intracellular signaling domain is located in the T cell membrane, and is used for transmitting signals to a T cell to stimulate the immune response of the T cell.

The CAR can target and recognize the target antigen on the surface of a tumor cell, so the T cell expressing the CAR can be used for targeting and killing a tumor cell. However, the existing T cell expressing the CAR is still weak in killing the tumor cell.

SUMMARY

The objective of the disclosure is to overcome the problem that the existing T cell expressing a CAR is still weak in killing a tumor cell, and to provide an anti-CD133 single-chain antibody.

In order to achieve the above objective, in a first aspect, the disclosure provides an anti-CD133 single-chain antibody, the amino acid sequence of which includes a sequence shown in SEQ ID NO. 1.

In a second aspect, the disclosure provides a nucleic acid encoding the anti-CD133 single-chain antibody according to the first aspect; and preferably, the nucleic acid has a nucleotide sequence shown in SEQ ID NO. 2.

In a third aspect, the disclosure provides a fusion protein containing an antigen binding domain, a transmembrane domain and an intracellular signaling domain that are sequentially linked; the amino acid sequence of the antigen binding domain includes the amino acid sequence of the anti-CD133 single-chain antibody according to the first aspect.

Preferably, the antigen binding domain includes the anti-CD133 single-chain antibody, and the intracellular signaling domain includes an anti-TIM3 single-chain antibody and/or IL7Rα or a truncated body of IL7Rα.

More preferably, the fusion protein has an amino acid sequence shown in any of SEQ ID NO. 3, SEQ ID NO. 4, SEQ ID NO. 5, or SEQ ID NO. 6.

In a fourth aspect, the disclosure provides a fusion nucleic acid encoding the fusion protein according to the third aspect.

Preferably, the fusion nucleic acid has a nucleotide sequence shown in any of SEQ ID NO. 7, SEQ ID NO. 8, SEQ ID NO. 9, or SEQ ID NO. 10.

In a fifth aspect, the disclosure provides an expression vector, the expression vector is inserted with an expression cassette, the expression cassette includes a first nucleic acid fragment encoding an antigen binding molecule and a second nucleic acid fragment encoding an intracellular signaling molecule, the antigen binding molecule contains the anti-CD133 single-chain antibody according to the first aspect, and an IRES element or a 2A peptide encoding sequence is inserted between the first nucleic acid fragment and the second nucleic acid fragment.

Preferably, the expression cassette is the fusion nucleic acid according to the fourth aspect.

In a sixth aspect, the disclosure provides a cell expressing a chimeric antigen receptor, the cell expressing a chimeric antigen receptor is obtained by transfection of the expression vector according to the fifth aspect by a host cell, and the chimeric antigen receptor contains the anti-CD133 single-chain antibody according to the first aspect.

Optionally, the host cell is a T cell.

In a seventh aspect, the disclosure provides use of the anti-CD133 single-chain antibody according to the first aspect, the nucleic acid according to the second aspect, the fusion protein according to the third aspect, the fusion nucleic acid according to the fourth aspect, the expression vector according to the fifth aspect, and the cell expressing a chimeric antigen receptor according to the sixth aspect in preparation of a drug for treating a tumor.

Optionally, the tumor is glioma.

In an eighth aspect, the disclosure provides a pharmaceutical composition, an active ingredient of which includes the cell expressing an anti-CD133 chimeric antigen receptor according to the sixth aspect.

According to the above technical solution, the anti-CD133 single-chain antibody provided by the disclosure can specifically recognize and bind a CD133 antigen on the surface of a tumor cell. Therefore, T lymphocytes expressing the anti-CD133 single-chain antibody can specifically kill CD133-positive tumor cells and have higher specificity and stronger killing ability.

Other features and advantages of the disclosure will be described in detail in the following specific embodiments.

BRIEF DESCRIPTION OF THE DRAWINGS

The accompanying drawings are intended to provide a further understanding of the disclosure, constitute a part of the description, and are used for interpreting the disclosure together with the following specific embodiments, rather than limiting the disclosure. In the figures.

DETAILED DESCRIPTION

Figure 1:
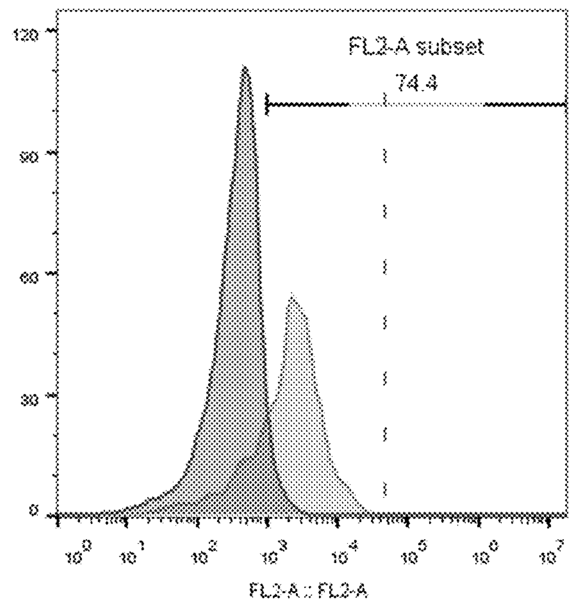
FIG. 1 is a flow cytometer test result diagram of CAR-T 1 cells according to an embodiment of the disclosure.

The specific embodiments of the disclosure will be described in detail below with reference to the accompanying drawings. It should be understood that the specific embodiments described herein are merely used for illustrating and interpreting the disclosure, rather than limiting the disclosure.

A first aspect of the disclosure provides an anti-CD133 single-chain antibody. The amino acid sequence of the anti-CD133 single-chain antibody includes a sequence shown in SEQ ID NO. 1.

The sequence shown in SEQ ID NO. 1 is as follows:

```
QVQLVQSGAEVKKPGASVKVSCKASGYTFTDFEMHWVRQAPGQGLEWMG
DIDPGTGDTAYNLKFKGRVTMTTDTSTSTAYMELRSLRSDDTAVYYCAL
GAFVYWGQGTLVTVSSGSTSGGGSGGGSGGGGSSDVVMTQSPLSLPVTP
GEPASISCRSSQSLANSYGNTYLSWYLQKPGQSPQLLIYGISNRFSGVP
DRFSGSGSGTDFTLKISRVEAEDVGVYYCLQGTHQPYTFGQGTKLEIK.
```

CD133 is a specific marker molecule expressed independently on the surface of various tumor stem cells, so CD133 can be used as a specific target for tumor therapy. The anti-CD133 single-chain antibody was designed against CD133, and chimeric antigen receptor T cells were constructed by using the designed anti-CD133 single-chain antibody and could specifically recognize and kill CD133-positive tumor cells.

The inventors of the disclosure found that the anti-CD133 single-chain antibody can specifically recognize and bind a CD133 antigen on the surface of a tumor cell. Therefore, T lymphocytes expressing the anti-CD133 single-chain antibody can specifically kill CD133-positive tumor cells and have higher specificity and stronger killing ability.

A second aspect of the disclosure provides a nucleic acid encoding the anti-CD133 single-chain antibody according to the first aspect. Preferably, the nucleic acid has a nucleotide sequence shown in SEQ ID NO. 2.

The nucleotide sequence shown in SEQ ID NO. 2 is as follows:

```
caggttcagctggtgcagtctggagctgaggtgaagaagcctggggcct
cagtgaaggtctcctgcaaggcttctggttacacctttaccgactttga
aatgcactgggtgcgacaggcccctggacaagggcttgagtggatggga
gatattgatcctggaactggtgatactgcctacaatctgaagttcaagg
gcagagtcaccatgaccacagacacatccacgagcacagcctacatgga
gctgaggagcctgaggtctgacgacacggccgtgtattactgtgcgttg
ggggcctttgtttactggggccagggaaccctggtcaccgtctcctcag
gcagtactagcggtggtggctccgggggcggttccggtgggggcggcag
cagcgatgttgtgatgactcagtctccactctccctgcccgtcacccct
ggagagccggcctccatctcctgcaggtctagtcagagtcttgcaaaca
gttatgggaacacctatttgtcttggtacctgcagaagccagggcagtc
tccacagctcctgatctatgggatttccaacagattttctggggtccct
gacaggttcagtggcagtggatcaggcacagattttacactgaaaatca
gcagagtggaggctgaggacgttggggtttattactgcttacaaggtac
acatcagccgtacacgtttggccaggggaccaagctggagatcaaa.
```

A third aspect of the disclosure provides a fusion protein containing an antigen binding domain, a transmembrane domain and an intracellular signaling domain that are sequentially linked; the amino acid sequence of the antigen binding domain includes the amino acid sequence of the anti-CD133 single-chain antibody according to the first aspect; preferably, the antigen binding domain includes the anti-CD133 single-chain antibody, and the intracellular signaling domain includes an anti-TIM3 single-chain antibody and/or IL7Rα or a truncated body of IL7Rα; and more preferably, the fusion protein has an amino acid sequence shown in any of SEQ ID NO. 3, SEQ ID NO. 4, SEQ ID NO. 5, or SEQ ID NO. 6.

The fusion protein shown in SEQ ID NO. 3 consists of the anti-CD133 single-chain antibody, a CD28, and a CD3. The amino acid sequence shown in SEQ ID NO. 3 is as follows:

```
QVQLVQSGAEVKKPGASVKVSCKASGYTFTDFEMHWVRQAPGQGLEWMG
DIDPGTGDTAYNLKFKGRVTMTTDTSTSTAYMELRSLRSDDTAVYYCAL
GAFVYWGQGTLVTVSSGSTSGGGSGGGSGGGGSSDVVMTQSPLSLPVTP
GEPASISCRSSQSLANSYGNTYLSWYLQKPGQSPQLLIYGISNRFSGVP
DRFSGSGSGTDFTLKISRVEAEDVGVYYCLQGTHQPYTFGQGTKLEIKT
TTPAPRPPTPAPTIASQPLSLRPEACRPAAGGAVHTRGLDFACDIYIWA
PLAGTCGVLLLSLVITLYCRSKRSRLLHSDYMNMTPRRPGPTRKHYQPY
APPRDFAAYRSRVKFSRSADAPAYKQGQNQLYNELNLGRREEYDVLDKR
RGRDPEMGGKPRRKNPQEGLYNELQKDKMAEAYSEIGMKGERRRGKGHD
GLYQGLSTATKDTYDALHMQALPPR.
```

The fusion protein shown in SEQ ID NO. 4 consists of the anti-CD133 single-chain antibody, a CD28, a truncated body of IL7Rα, and a CD3. The amino acid sequence shown in SEQ ID NO. 4 is as follows:

```
QVQLVQSGAEVKKPGASVKVSCKASGYTFTDFEMHWVRQAPGQGLEWMG
DIDPGTGDTAYNLKFKGRVTMTTDTSTSTAYMELRSLRSDDTAVYYCAL
GAFVYWGQGTLVTVSSGSTSGGGSGGGSGGGGSSDVVMTQSPLSLPVTP
GEPASISCRSSQSLANSYGNTYLSWYLQKPGQSPQLLIYGISNRFSGVP
DRFSGSGSGTDFTLKISRVEAEDVGVYYCLQGTHQPYTFGQGTKLEIKT
TTPAPRPPTPAPTIASQPLSLRPEACRPAAGGAVHTRGLDFACDIYIWA
PLAGTCGVLLLSLVITLYCRSKRSRLLHSDYMNMTPRRPGPTRKHYQPY
APPRDFAAYRSKKRIKPIVWPSLPDHKKTLEHLCKKPRKNLNVSFNPES
FLDCQIHRVDDIQARDEVEGFLQDTFPQQLEESEKQRLLGSNQEEAYVT
MSSFYQNQRVKFSRSADAPAYKQGQNQLYNELNLGRREEYDVLDKRRGR
DPEMGGKPRRKNPQEGLYNELQKDKMAEAYSEIGMKGERRRGKGHDGLY
QGLSTATKDTYDALHMQALPPR.
```

The fusion protein shown in SEQ ID NO. 5 consists of the anti-CD133 single-chain antibody, a CD28, a CD3, a T2A, and an anti-TIM3 single-chain antibody. The amino acid sequence shown in SEQ ID NO. 5 is as follows:

```
QVQLVQSGAEVKKPGASVKVSCKASGYTFTDFEMHWVRQAPGQGLEWMG
DIDPGTGDTAYNLKFKGRVTMTTDTSTSTAYMELRSLRSDDTAVYYCAL
```

-continued

```
GAFVYWGQGTLVTVSSGSTSGGGSGGGSGGGGSSDVVMTQSPLSLPVTP
GEPASISCRSSQSLANSYGNTYLSWYLQKPGQSPQLLIYGISNRFSGVP
DRFSGSGSGTDFTLKISRVEAEDVGVYYCLQGTHQPYTFGQGTKLEIKT
TTPAPRPPTPAPTIASQPLSLRPEACRPAAGGAVHTRGLDFACDIYIWA
PLAGTCGVLLLSLVITLYCRSKRSRLLHSDYMNMTPRRPGPTRKHYQPY
APPRDFAAYRSRVKFSRSADAPAYKQGQNQLYNELNLGRREEYDVLDKR
RGRDPEMGGKPRRKNPQEGLYNELQKDKMAEAYSEIGMKGERRRGKGHD
GLYQGLSTATKDTYDALHMQALPPREGRGSLLTCGDVEENPGPMTNKCL
LQIALLLCFSTTALSQVQLQQSGPGLVKPSHTLSLTCTVSGGSISSGGY
YWSWTRQHPGMGLEWIGYISYSGSIYYTPSLKSRLTISVDTSKNQFSLK
LSSVTAADTAVYYCASLDSWGSNRDYWGQGTLVTVSSGGGGSEIVLTQS
PATLSLSPGERATLSCRASQSVSSYLAWYQQKPGQAPRLLIYDASNRAT
GIPARFSGSGSGTDFTLTISSLEPEDFAVYYCQQRSNWPLTFGGGTKVE
IK.
```

The fusion protein shown in SEQ ID NO. 6 consists of the anti-CD133 single-chain antibody, a CD28, a truncated body of IL7Rα, a CD3, a T2A, and an anti-TIM3 single-chain antibody. The amino acid sequence shown in SEQ ID NO. 6 is as follows:

```
QVQLVQSGAEVKKPGASVKVSCKASGYTFTDFEMHWVRQAPGQGLEWMG
DIDPGTGDTAYNLKFKGRVTMTTDTSTSTAYMELRSLRSDDTAVYYCAL
GAFVYWGQGTLVTVSSGSTSGGGSGGGSGGGGSSDVVMTQSPLSLPVTP
GEPASISCRSSQSLANSYGNTYLSWYLQKPGQSPQLLIYGISNRFSGVP
DRFSGSGSGTDFTLKISRVEAEDVGVYYCLQGTHQPYTFGQGTKLEIKT
TTPAPRPPTPAPTIASQPLSLRPEACRPAAGGAVHTRGLDFACDIYIWA
PLAGTCGVLLLSLVITLYCRSKRSRLLHSDYMNMTPRRPGPTRKHYQPY
APPRDFAAYRSKKRIKPIVWPSLPDHKKTLEHLCKKPRKNLNVSFNPES
FLDCQIHRVDDIQARDEVEGFLQDTFPQQLEESEKQRLLGSNQEEAYVT
MSSFYQNQRVKFSRSADAPAYKQGQNQLYNELNLGRREEYDVLDKRRGR
DPEMGGKPRRKNPQEGLYNELQKDKMAEAYSEIGMKGERRRGKGHDGLY
QGLSTATKDTYDALHMQALPPREGRGSLLTCGDVEENPGPMTNKCLLQI
ALLLCFSTTALSQVQLQQSGPGLVKPSHTLSLTCTVSGGSISSGGYYWS
WTRQHPGMGLEWIGYISYSGSIYYTPSLKSRLTISVDTSKNQFSLKLSS
VTAADTAVYYCASLDSWGSNRDYWGQGTLVTVSSGGGGSEIVLTQSPAT
LSLSPGERATLSCRASQSVSSYLAWYQQKPGQAPRLLIYDASNRATGIP
ARFSGSGSGTDFTLTISSLEPEDFAVYYCQQRSNWPLTFGGGTKVEIK.
```

A fourth aspect of the disclosure provides a fusion nucleic acid encoding the fusion protein according to the third aspect; and preferably, the fusion nucleic acid has a nucleotide sequence shown in any of SEQ ID NO. 7, SEQ ID NO. 8, SEQ ID NO. 9, or SEQ ID NO. 10.

The nucleotide sequence shown in SEQ ID NO. 7 is used for encoding the amino acid sequence shown in SEQ ID NO. 3. The nucleotide sequence shown in SEQ ID NO. 7 is as follows:

```
caggttcagctggtgcagtctggagctgaggtgaagaagcctggggcct
cagtgaaggtctcctgcaaggcttctggttacacctttaccgactttga
aatgcactgggtgcgacaggcccctggacaagggcttgagtggatggga
gatattgatcctggaactggtgatactgcctacaatctgaagttcaagg
gcagagtcaccatgaccacagacacatccacgagcacagcctacatgga
gctgaggagcctgaggtctgacgacacggccgtgtattactgtgcgttg
ggggcctttgtttactggggccagggaaccctggtcaccgtctcctcag
gcagtactagcggtggtggctccgggggcggttccggtgggggcggcag
cagcgatgttgtgatgactcagtctccactctccctgcccgtcacccct
ggagagccggcctccatctcctgcaggtctagtcagagtcttgcaaaca
gttatgggaacacctatttgtcttggtacctgcagaagccagggcagtc
tccacagctcctgatctatgggatttccaacagattttctggggtccct
gacaggttcagtggcagtggatcaggcacagattttacactgaaaatca
gcagagtggaggctgaggacgttggggtttattactgcttacaaggtac
acatcagccgtacacgtttggccaggggaccaagctggagatcaaaacc
actaccccagcaccgaggccacccaccccggctcctaccatcgcctccc
agcctctgtccctgcgtccggaggcatgtagacccgcagctggtggggc
cgtgcatacccggggtcttgacttcgcctgcgatatctacatttgggcc
cctctggctggtacttgcggggtcctgctgctttcactcgtgatcactc
tttactgtaggagtaagaggagcaggctcctgcacagtgactacatgaa
catgactccccgccgccccgggcccacccgcaagcattaccagccctat
gccccaccacgcgacttcgcagcctatcgctcccgcgtgaaattcagcc
gcagcgcagatgctccagcctacaagcaggggcagaaccagctctacaa
cgaactcaatcttggtcggagagaggagtacgacgtgctggacaagcgg
agaggacgggacccagaaatgggcgggaagccgcgcagaaagaatcccc
aagagggcctgtacaacgagctccaaaaggataagatggcagaagccta
tagcgagattggtatgaaaggggaacgcagaagaggcaaaggccacgac
ggactgtaccagggactcagcaccgccaccaaggacacctatgacgctc
ttcacatgcaggccctgccgcctcgg.
```

The nucleotide sequence shown in SEQ ID NO. 8 is used for encoding the amino acid sequence shown in SEQ ID NO. 4. The nucleotide sequence shown in SEQ ID NO. 8 is as follows:

```
caggttcagctggtgcagtctggagctgaggtgaagaagcctggggcct
cagtgaaggtctcctgcaaggcttctggttacacctttaccgactttga
aatgcactgggtgcgacaggcccctggacaagggcttgagtggatggga
gatattgatcctggaactggtgatactgcctacaatctgaagttcaagg
gcagagtcaccatgaccacagacacatccacgagcacagcctacatgga
gctgaggagcctgaggtctgacgacacggccgtgtattactgtgcgttg
ggggcctttgtttactggggccagggaaccctggtcaccgtctcctcag
gcagtactagcggtggtggctccgggggcggttccggtgggggcggcag
```

-continued cagcgatgttgtgatgactcagtctccactctccctgcccgtcacccct
ggagagccggcctccatctcctgcaggtctagtcagagtcttgcaaaca
gttatgggaacacctatttgtcttggtacctgcagaagccagggcagtc
tccacagctcctgatctatgggatttccaacagattttctggggtccct
gacaggttcagtggcagtggatcaggcacagattttacactgaaaatca
gcagagtggaggctgaggacgttggggtttattactgcttacaaggtac
acatcagccgtacacgtttggccaggggaccaagctggagatcaaaacc
actaccccagcaccgaggccacccaccccggctcctaccatcgcctccc
agcctctgtccctgcgtccggaggcatgtagacccgcagctggtggggc
cgtgcatacccggggtcttgacttcgcctgcgatatctacatttgggcc
cctctggctggtacttgcggggtcctgctgctttcactcgtgatcactc
tttactgtaggagtaagaggagcaggctcctgcacagtgactacatgaa
catgactccccgccgccccgggcccacccgcaagcattaccagccctat
gccccaccacgcgacttcgcagcctatcgctccaaaaaaaggattaagc
ctatcgtatggcccagtctccccgatcacaagaagactctggaacacct
ttgtaagaaaccaagaaaaaatttaaatgtgagtttcaatcctgaaagt
ttcctggactgccagattcatagggtggatgacattcaagctagagatg
aagtggaaggttttctgcaagatacgtttcctcagcaactagaagaatc
tgagaagcagaggcttctgggatcaaatcaagaagaagcatatgtcacc
atgtccagcttctaccaaaaccagcgcgtgaaattcagccgcagcgcag
atgctccagcctacaagcaggggcagaaccagctctacaacgaactcaa
tcttggtcggagagaggagtacgacgtgctggacaagcggagaggacgg
gacccagaaatgggcgggaagccgcgcagaaagaatccccaagagggcc
tgtacaacgagctccaaaaggataagatggcagaagcctatagcgagat
tggtatgaaaggggaacgcagaagaggcaaaggccacgacggactgtac
cagggactcagcaccgccaccaaggacacctatgacgctcttcacatgc
aggccctgccgcctcgg.

The nucleotide sequence shown in SEQ ID NO. 9 is used for encoding the amino acid sequence shown in SEQ ID NO. 5. The nucleotide sequence shown in SEQ ID NO. 9 is as follows:

caggttcagctggtgcagtctggagctgaggtgaagaagcctggggcct
cagtgaaggtctcctgcaaggcttctggttacacctttaccgactttga
aatgcactgggtgcgacaggcccctggacaagggcttgagtggatggga
gatattgatcctggaactggtgatactgcctacaatctgaagttcaagg
gcagagtcaccatgaccacagacacatccacgagcacagcctacatgga
gctgaggagcctgaggtctgacgacacggccgtgtattactgtgcgttg
ggggcctttgtttactggggccagggaaccctggtcaccgtctcctcag
gcagtactagcggtggtggctccgggggcggttccggtgggggcggcag
cagcgatgttgtgatgactcagtctccactctccctgcccgtcacccct
ggagagccggcctccatctcctgcaggtctagtcagagtcttgcaaaca
gttatgggaacacctatttgtcttggtacctgcagaagccagggcagtc
tccacagctcctgatctatgggatttccaacagattttctggggtccct
gacaggttcagtggcagtggatcaggcacagattttacactgaaaatca
gcagagtggaggctgaggacgttggggtttattactgcttacaaggtac
acatcagccgtacacgtttggccaggggaccaagctggagatcaaaacc
actaccccagcaccgaggccacccaccccggctcctaccatcgcctccc
agcctctgtccctgcgtccggaggcatgtagacccgcagctggtggggc
cgtgcatacccggggtcttgacttcgcctgcgatatctacatttgggcc
cctctggctggtacttgcggggtcctgctgctttcactcgtgatcactc
tttactgtaggagtaagaggagcaggctcctgcacagtgactacatgaa
catgactccccgccgccccgggcccacccgcaagcattaccagccctat
gccccaccacgcgacttcgcagcctatcgctcccgcgtgaaattcagcc
gcagcgcagatgctccagcctacaagcaggggcagaaccagctctacaa
cgaactcaatcttggtcggagagaggagtacgacgtgctggacaagcgg
agaggacgggacccagaaatgggcgggaagccgcgcagaaagaatcccc
aagagggcctgtacaacgagctccaaaaggataagatggcagaagccta
tagcgagattggtatgaaaggggaacgcagaagaggcaaaggccacgac
ggactgtaccagggactcagcaccgccaccaaggacacctatgacgctc
ttcacatgcaggccctgccgcctcgggagggaaggggttctctcctgac
ctgcggcgatgtggaggagaaccccggacccatgaccaacaagtgtctc
ctccaaattgctctcctgttgtgcttctccactacagctctttcccagg
tgcagctacagcagtcgggcccaggactggtgaagccttcacacaccct
gtccctcacctgcactgtctctggtggctccatcagcagtggtggttac
tactggagttggacccgtcagcacccagggatgggcctggagtggattg
gatacatctcttacagtgggagtatctattacactccgtccctcaagag
tcgacttaccatatcagtggacacgtctaagaaccagttctccctgaag
ctgagctctgtgactgccgcggacacggccgtatattactgtgcgagtt
tggattcctggggatctaaccgtgactactggggccagggaaccctggt
caccgtctcgagtggaggtggtggatccgaaattgtgttgacgcagtct
ccagccaccctgtctttgtctccaggggaaagagccaccctctcctgca
gggccagtcagagtgttagcagctacttagcctggtaccaacagaaacc
tggccaggctcccaggctcctcatctatgatgcatccaacagggccact
ggcatcccagccaggttcagtggcagtgggtctgggacagacttcactc
tcaccatcagcagcctagagcctgaagattttgcagtttattactgtca
gcagcgtagcaactggccgctcactttcggcggagggaccaaggtggag
attaag.

The nucleotide sequence shown in SEQ ID NO. 10 is used for encoding the amino acid sequence shown in SEQ ID NO. 6. The nucleotide sequence shown in SEQ ID NO. 10 is as follows:

```
caggttcagctggtgcagtctggagctgaggtgaagaagcctggggcct
cagtgaaggtctcctgcaaggcttctggttacacctttaccgactttga
aatgcactgggtgcgacaggcccctggacaagggcttgagtggatggga
gatattgatcctggaactggtgatactgcctacaatctgaagttcaagg
gcagagtcaccatgaccacagacacatccacgagcacagcctacatgga
gctgaggagcctgaggtctgacgacacggccgtgtattactgtgcgttg
gggcctttgtttactggggccagggaaccctggtcaccgtctcctcag
gcagtactagcggtggtggctccgggggcggttccggtgggggcggcag
cagcgatgttgtgatgactcagtctccactctccctgcccgtcacccct
ggagagccggcctccatctcctgcaggtctagtcagagtcttgcaaaca
gttatgggaacacctatttgtcttggtacctgcagaagccagggagtct
ccacagctcctgatctatgggatttccaacagattttctggggtccctg
acaggttcagtggcagtggatcaggcacagattttacactgaaaatcag
cagagtggaggctgaggacgttggggtttattactgcttacaaggtaca
catcagccgtacacgtttggccaggggaccaagctggagatcaaaacca
ctaccccagcaccgaggccacccaccccggctcctaccatcgcctccca
gcctctgtccctgcgtccggaggcatgtagacccgcagctggtggggcc
gtgcatacccggggtcttgacttcgcctgcgatatctacatttgggccc
ctctggctggtacttgcggggtcctgctgctttcactcgtgatcactct
ttactgtaggagtaagaggagcaggctcctgcacagtgactacatgaac
atgactccccgccgccccgggcccacccgcaagcattaccagccctatg
ccccaccacgcgacttcgcagcctatcgctccaaaaaaaggattaagcc
tatcgtatggcccagtctccccgatcacaagaagactctggaacacctt
tgtaagaaaccaagaaaaaatttaaatgtgagtttcaatcctgaaagtt
tcctggactgccagattcatagggtggatgacattcaagctagagatga
agtggaaggttttctgcaagatacgtttcctcagcaactagaagaatct
gagaagcagaggcttctgggatcaaatcaagaagaagcatatgtcacca
tgtccagcttctaccaaaaccagcgcgtgaaattcagccgcagcgcaga
tgctccagcctacaagcaggggcagaaccagctctacaacgaactcaat
cttggtcggagagaggagtacgacgtgctggacaagcggagaggacggg
acccagaaatgggcgggaagccgcgcagaaagaatccccaagagggcct
gtacaacgagctccaaaaggataagatggcagaagcctatagcgagatt
ggtatgaaaggggaacgcagaagaggcaaaggccacgacggactgtacc
agggactcagcaccgccaccaaggacacctatgacgctcttcacatgca
ggccctgccgcctcgggagggaaggggttctctcctgacctgcggcgat
gtggaggagaaccccggacccatgaccaacaagtgtctcctccaaattg
ctctcctgttgtgcttctccactacagctctttcccaggtgcagctaca
gcagtcgggcccaggactggtgaagccttcacacaccctgtccctcacc
tgcactgtctctggtggctccatcagcagtggtggttactactggagtt
ggacccgtcagcacccagggatgggcctggagtggattggatacatctc
ttacagtgggagtatctattacactccgtccctcaagagtcgacttacc
```

-continued

```
atatcagtggacacgtctaagaaccagttctccctgaagctgagctctg
tgactgccgcggacacggccgtatattactgtgcgagtttggattcctg
gggatctaaccgtgactactggggccagggaaccctggtcaccgtctcg
agtggaggtggtggatccgaaattgtgttgacgcagtctccagccaccc
tgtctttgtctccaggggaaagagccaccctctcctgcagggccagtca
gagtgttagcagctacttagcctggtaccaacagaaacctggccaggct
cccaggctcctcatctatgatgcatccaacagggccactggcatcccag
ccaggttcagtggcagtgggtctgggacagacttcactctcaccatcag
cagcctagagcctgaagattttgcagtttattactgtcagcagcgtagc
aactggccgctcactttcggcggagggaccaaggtggagattaagcgct
cactttcggcggagggaccaaggtggagattaag.
```

A fifth aspect of the disclosure provides an expression vector, the expression vector is inserted with an expression cassette, the expression cassette includes a first nucleic acid fragment encoding an antigen binding molecule and a second nucleic acid fragment encoding an intracellular signaling molecule, the antigen binding molecule contains the anti-CD133 single-chain antibody according to the first aspect, and an IRES element or a 2A peptide encoding sequence is inserted between the first nucleic acid fragment and the second nucleic acid fragment; and preferably, the expression cassette is the fusion nucleic acid according to the fourth aspect.

A sixth aspect of the disclosure provides a cell expressing a chimeric antigen receptor, the cell expressing a chimeric antigen receptor is obtained by transfection of the expression vector according to the fifth aspect by a host cell, and the chimeric antigen receptor contains the anti-CD133 single-chain antibody according to the first aspect. Optionally, the host cell is a T cell.

A seventh aspect of the disclosure provides use of the anti-CD133 single-chain antibody according to the first aspect, the nucleic acid according to the second aspect, the fusion protein according to the third aspect, the fusion nucleic acid according to the fourth aspect, the expression vector according to the fifth aspect, and the cell expressing a chimeric antigen receptor according to the sixth aspect in preparation of a drug for treating a tumor. Optionally, the tumor is glioma.

An eighth aspect of the disclosure provides a pharmaceutical composition, an active ingredient of which includes the cell expressing an anti-CD133 chimeric antigen receptor according to the sixth aspect.

The disclosure is further described by the following examples, but the disclosure is not limited thereby.

Example 1

This example was used to explain the construction of expression vectors.

(1) Nucleotide sequences shown in SEQ ID NO. 7 to 10 were respectively synthesized by using a full sequence synthesis method. The nucleotide sequences shown in SEQ ID NO. 7 to 10 were used for encoding fusion proteins shown in SEQ ID NO. 3 to 6. The compositions of the fusion proteins shown in SEQ ID NO. 3 to 6 were as follows:

G1: the fusion protein shown in SEQ ID NO. 3 consisted of an anti-CD133 single-chain antibody, a CD28, and a CD3;

G2: the fusion protein shown in SEQ ID NO. 4 consisted of an anti-CD133 single-chain antibody, a CD28, a truncated body of IL7Rα, and a CD3;

G3: the fusion protein shown in SEQ ID NO. 5 consisted of an anti-CD133 single-chain antibody, a CD28, a CD3, a T2A, and an anti-TIM3 single-chain antibody;

G4: the fusion protein shown in SEQ ID NO. 6 consisted of an anti-CD133 single-chain antibody, a CD28, a truncated body of IL7Rα, a CD3, a T2A, and an anti-TIM3 single-chain antibody.

(2) The four kinds of nucleotide sequences synthesized in step (1) were respectively inserted into pLVX-IRES-ΔNGFR (purchased from Clontech Company, item number 631982) as a vector to obtain four kinds of lentivirus expression vectors of this example.

Example 2

This example was used to explain the preparation and test of T cells expressing an anti-CD133 single-chain antibody.

(1) The four kinds of lentivirus expression vectors constructed in Example 1 and an empty pLVX-IRES-ΔNGFR vector were packaged with lentiviruses respectively, and then T cells were cultured in vitro, transfected and proliferated according to the following methods.

(2) T cells in blood were separated according to the following method: 1 mL of sterile PBS and 1 mL of blood were mixed evenly, then slowly added to an upper layer of a lymphocyte separation medium Ficoll, and centrifuged at 4° C. and 400 g for 30 min, with acceleration and deceleration set to 0 respectively. After centrifugation, the upper plasma was removed, the middle white membrane cells were pipetted, PBS was added for re-suspension washing, and centrifugation was carried out for 10 min at 100 g, with normal acceleration and deceleration. After centrifugation, the upper washing solution was removed, 1 mL of 1640+10% FBS+1% double antibody+1×Glutamine medium was added to re-suspend cells, and then the cells were stimulated to proliferate by means of anti-human CD3/CD28 magnetic beads (purchased from Thermo Fisher company), where the concentration of re-suspended cells was $1\times10^6$ cells/mL and the amount of magnetic beads added was 100 μL. Then 100 IU/mL rhIL-2 (Peprotech) was added to stimulate culture for 2 days to obtain T cells.

(3) Transfection of lentiviruses was carried out according to the following method: the lentiviruses packaged in step (1) were respectively added to five parts of T cells separated above, and then polybrene with a final concentration of 6 μg/mL was added, followed by uniform mixing and centrifugation at 32° C. and 800 g for 100 min. After centrifugation, the culture was continued in an incubator for 24 h. After the culture, the culture solution was centrifuged at 1500 rpm for 15 min, and the centrifuged cells were inoculated at a density of $1\times10^6$/mL into a culture plate and stimulated for culture with rhIL2-100 IU/mL. After that, the medium was changed every 2-3 days until 2-4 weeks, and transfected T lymphocytes CAR-T 1, CAR-T 2, CAR-T 3, CAR-T 4, and CAR-T 5 were obtained. CAR-T 1 was transfected with the nucleotide sequence shown in SEQ ID NO. 7 and could express the fusion protein shown in SEQ ID NO. 3; CAR-T 2 was transfected with the nucleotide sequence shown in SEQ ID NO. 8 and could express the fusion protein shown in SEQ ID NO. 4; CAR-T 3 was transfected with the nucleotide sequence shown in SEQ ID NO. 9 and could express the fusion protein shown in SEQ ID NO. 5; CAR-T 4 was transfected with the nucleotide sequence shown in SEQ ID NO. 10 and could express the fusion protein shown in SEQ ID NO. 6; and CAR-T 5 was transfected with the empty vector.

After culture, the cells were re-suspended with PBS, and the ratio of the above five kinds of transfected T lymphocytes and the expression of CAR protein on the surface were tested with a flow cytometer. The test method was as follows: the T cells to be tested after transfection were centrifuged and collected respectively, the supernatant was discarded after the T cells to be tested were washed with PBS once, and a corresponding test amount of monoclonal antibody was added according to antibody instructions and kept away from light for 30 min, followed by PBS washing, re-suspension, filtration with a membrane, and test with a flow cytometer, where the antibody used for the test was a PE labeled goat anti-human VH+VL flow antibody. The results were shown in FIGS. 1-5.

Figure 2:
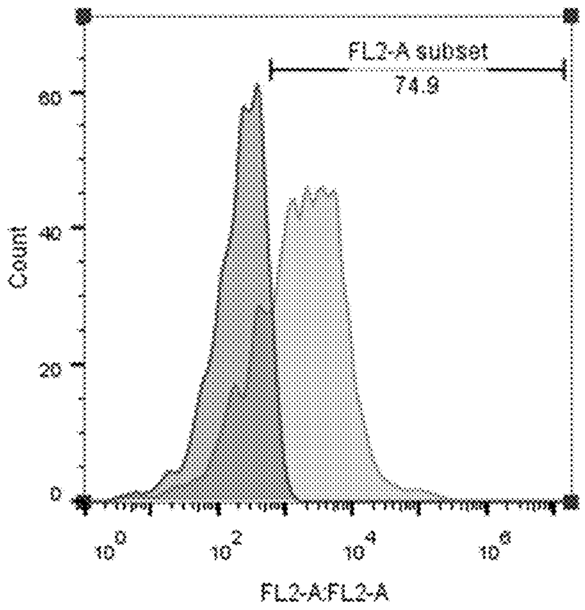
FIG. 2 is a flow cytometer test result diagram of CAR-T 2 cells according to an embodiment of the disclosure.
Figure 3:
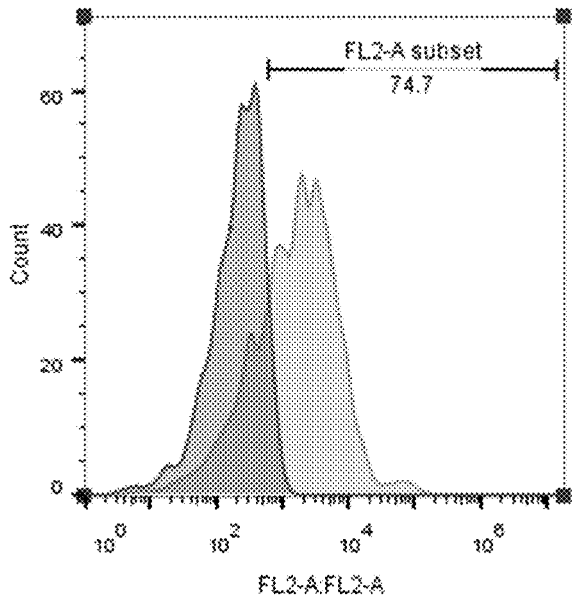
FIG. 3 is a flow cytometer test result diagram of CAR-T 3 cells according to an embodiment of the disclosure.
Figure 4:
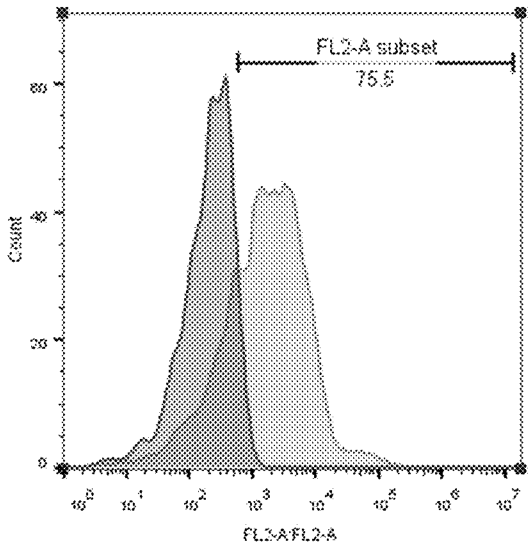
FIG. 4 is a flow cytometer test result diagram of CAR-T 4 cells according to an embodiment of the disclosure.
Figure 5:
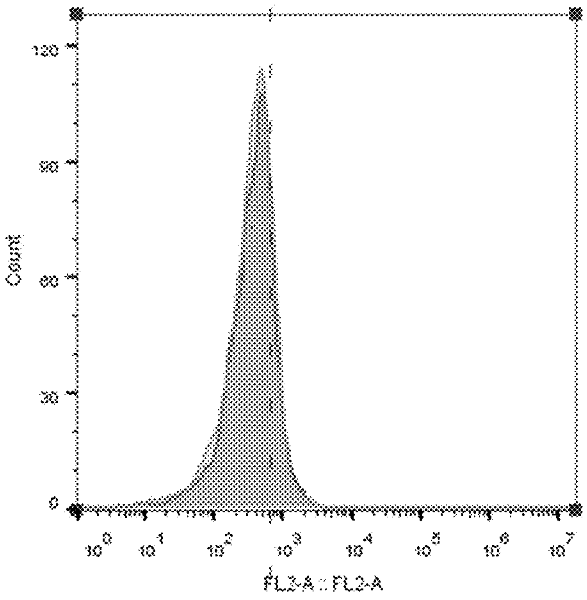
FIG. 5 is a flow cytometer test result diagram of CAR-T 5 cells according to an embodiment of the disclosure.

FIG. 1 is a flow cytometer test result diagram of CAR-T 1 cells provided by an embodiment of the disclosure;

FIG. 2 is a flow cytometer test result diagram of CAR-T 2 cells provided by an embodiment of the disclosure;

FIG. 3 is a flow cytometer test result diagram of CAR-T 3 cells provided by an embodiment of the disclosure;

FIG. 4 is a flow cytometer test result diagram of CAR-T 4 cells provided by an embodiment of the disclosure; and FIG. 5 is a flow cytometer test result diagram of CAR-T 5 cells according to an embodiment of the disclosure.

As can be seen from FIGS. 1-4, other cells different from normal T lymphocytes were detected out from the CAR-T 1 cells, the CAR-T 2 cells, the CAR-T 3 cells, and the CAR-T 4 cells. As can be seen from FIG. 5, other cells different from normal T lymphocytes were not detected out from the CAR-T 5 cells. This showed that the CAR-T cells transfected with fusion genes in this example had successfully expressed the target fusion protein.

Example 3

This example was used to verify the ability of T cells expressing an anti-CD133 single-chain antibody to kill CD133-positive tumor cells.

Kits for LDH release tests in this example were purchased from DOJINDO.

The five kinds of CAR-T cells obtained by transfection and culture in Example 2 were respectively mixed with CD44- and CD133-positive glioma stem cells GSC20 according to different effect-target ratios (the number of T cells: the number of glioma stem cells). The mixed cells were cultured in 96-well plates, where each well contained $4\times10^4$ glioma stem cells, and the reaction system was 200 μL per well. The culture conditions included: 37° C., 5% $CO_2$, and culture in a saturated humidity incubator for 4 h.

Determination of lactate dehydrogenase activity: after centrifugation, 100 μL of supernatant was pipetted from each well and placed in 96-well enzyme-labeled plates, 100 μL of LDH substrate was added to each well, and the reaction was carried out at room temperature for 30 min without light. After the reaction, 50 μL of termination solution was added to each well to terminate the enzymatic reaction. The optical density (OD) was measured with a microplate reader 490 nm. The average optical density (OD) of each group was calculated, and the lysis rate of glioma stem cells by each kind of T cells was calculated according to the following formula. The results were shown in Table 1.

Lysis rate %=(OD of the experimental group−OD spontaneously released by glioma stem cells−OD naturally released by effector cells)/(maximum OD released by glioma stem cells−OD spontaneously released by glioma stem cells)

TABLE 1

| | Lysis rate of glioma stem cells by CAR-T cells under different effect-target ratios (%) | | | |
|---|---|---|---|---|
| CAR-T cells | 5:1 | 3:1 | 2:1 | 1:1 |
| CAR-T 1 | 41.36% | 33.52% | 25.99% | 6.53% |
| CAR-T 2 | 43.35% | 39.65% | 28.01% | 16.30% |
| CAR-T 3 | 49.47% | 35.26% | 20.34% | 16.91% |
| CAR-T 4 | 87.24% | 69.58% | 36.79% | 31.41% |
| CAR-T 5 | 6.87% | 2.63% | 1.23% | 2.41% |

As can be seen from Table 1, T lymphocytes expressing the anti-CD133 single-chain antibody provided by the disclosure can specifically kill CD133-positive tumor cells and have higher specificity and stronger killing ability.

Comparative Example

Conventional second generation CAR-T cells (EGFR vIII-CD28-CD3) targeting a classical tumor target EGFR vIII were used to replace the T cells in Example 3, and then killing rates of glioma stem cells GSC20 by CAR-T under different effect-target ratios were tested according to the method of Example 3. The test result is shown in Table 2.

TABLE 2

| | Lysis rate of glioma stem cells by conventional second generation CAR-T cells under different effect-target ratios (%) | | | |
|---|---|---|---|---|
| Effect-target ratio | 5:1 | 3:1 | 2:1 | 1:1 |
| Conventional CAR-T | 17.57% | 14.62% | 13.97% | 11.88% |

As can be seen from Table 2, the ability of the conventional second generation CAR-T cells targeting a classical tumor stem cell target EGFR vIII to kill glioma stem cells was weaker than that of the T cells expressing the anti-CD133 single-chain antibody provided by the disclosure.

The preferred embodiments of the disclosure are described in detail above with reference to the accompanying drawings. However, the disclosure is not limited to the specific details in the above embodiments. Various simple variations may be made to the technical solutions of the disclosure within the scope of the technical idea of the disclosure, and these simple variations fall within the scope of the disclosure.

It should be further noted that the specific technical features described in the above specific embodiments may be combined in any suitable manner without contradiction. In order to avoid unnecessary repetition, the disclosure will not describe various possible combinations.

Moreover, the various different embodiments of the disclosure may be combined randomly without deviating from the idea of the disclosure, and the combinations should also be regarded as the disclosure of the disclosure.

What is claimed is:

1. An anti-CD133 single-chain antibody, wherein the amino acid sequence of the anti-CD133 single-chain antibody consists of a sequence shown in SEQ ID NO. 1.

2. A nucleic acid, wherein the nucleic acid encodes the anti-CD133 single-chain antibody according to claim 1.

3. A fusion protein, wherein the fusion protein contains an antigen binding domain and an intracellular signaling domain; wherein the amino acid sequence of the antigen binding domain comprises the amino acid sequence of the anti-CD133 single-chain antibody according to claim 1.

4. A fusion nucleic acid, wherein the fusion nucleic acid encodes the fusion protein according to claim 3.

5. An expression vector, wherein the expression vector is inserted with an expression cassette, the expression cassette comprises a first nucleic acid fragment encoding an antigen binding molecule and a second nucleic acid fragment encoding an intracellular signaling molecule, the antigen binding molecule contains the anti-CD133 single-chain antibody according to claim 1, and an IRES element or a 2A peptide encoding sequence is inserted between the first nucleic acid fragment and the second nucleic acid fragment.

6. A cell expressing a chimeric antigen receptor, wherein the cell expressing a chimeric antigen receptor is obtained by transfection of the expression vector according to claim 5 into a host cell, and the chimeric antigen receptor contains an anti-CD133 single-chain antibody, wherein the amino acid sequence of the anti-CD133 single-chain antibody consists of a sequence shown in SEQ ID NO. 1.

7. The cell according to claim 6, wherein the host cell is a T cell.

8. A pharmaceutical composition, wherein an active ingredient of the pharmaceutical composition comprises the cell expressing an anti-CD133 chimeric antigen receptor according to claim 6.

9. The nucleic acid according to claim 2, wherein the nucleic acid has a nucleotide sequence shown in SEQ ID NO. 2.

10. The fusion protein according to claim 3, wherein the antigen binding domain comprises the anti-CD133 single-chain antibody.

11. The fusion protein according to claim 3, wherein the fusion protein has an amino acid sequence shown in any of SEQ ID NO. 3, SEQ ID NO. 4, SEQ ID NO. 5, or SEQ ID NO. 6.

12. The fusion nucleic acid according to claim 4, wherein the fusion nucleic acid has a nucleotide sequence shown in any of SEQ ID NO. 7, SEQ ID NO. 8, SEQ ID NO. 9, or SEQ ID NO. 10.

13. The expression vector according to claim 5, wherein the expression cassette is a fusion nucleic acid, wherein the fusion nucleic acid encodes a fusion protein, wherein the fusion protein contains an antigen binding domain, a transmembrane domain and an intracellular signaling domain that are sequentially linked; the amino acid sequence of the antigen binding domain comprises the amino acid sequence of an anti-CD133 single-chain antibody, wherein the amino acid sequence of the anti-CD133 single-chain antibody comprises a sequence shown in SEQ ID NO. 1.

14. The fusion protein according to claim 3, wherein the fusion protein further comprising a transmembrane domain, wherein the antigen binding domain, the transmembrane domain, and the intracellular signaling domain are sequentially linked.

15. The fusion protein according to claim 3, wherein the intracellular signaling domain comprises IL7Rα or a truncated body of IL7Rα;

and wherein the truncated body of IL7Rα is the IL7Rα fragment from the fusion protein of SEQ ID NO: 4.

16. The fusion protein according to claim 3, further comprising an anti-TIM3 single-chain antibody.

* * * * *

SEQUENCE LISTING

```
<160> NUMBER OF SEQ ID NOS: 10

<210> SEQ ID NO 1
<211> LENGTH: 244
<212> TYPE: PRT
<213> ORGANISM: Artificial Sequence
<220> FEATURE:
<223> OTHER INFORMATION: This sequence is synthesized in lab.

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Glu Met His Trp Val Arg Gln Ala Pro Gly Gln Gly Leu Glu Trp Met
        35                  40                  45

Gly Asp Ile Asp Pro Gly Thr Gly Asp Thr Ala Tyr Asn Leu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Leu Gly Ala Phe Val Tyr Trp Gly Gln Gly Thr Leu Val Thr Val
            100                 105                 110

Ser Ser Gly Ser Thr Ser Gly Gly Gly Ser Gly Gly Gly Ser Gly Gly
        115                 120                 125
```

```
Gly Gly Ser Ser Asp Val Val Met Thr Gln Ser Pro Leu Ser Leu Pro
    130                 135                 140

Val Thr Pro Gly Glu Pro Ala Ser Ile Ser Cys Arg Ser Ser Gln Ser
145                 150                 155                 160

Leu Ala Asn Ser Tyr Gly Asn Thr Tyr Leu Ser Trp Tyr Leu Gln Lys
                165                 170                 175

Pro Gly Gln Ser Pro Gln Leu Leu Ile Tyr Gly Ile Ser Asn Arg Phe
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Glu Asp Val Gly Val Tyr Tyr
    210                 215                 220

Cys Leu Gln Gly Thr His Gln Pro Tyr Thr Phe Gly Gln Gly Thr Lys
225                 230                 235                 240

Leu Glu Ile Lys


<210> SEQ ID NO 2
<211> LENGTH: 732
<212> TYPE: DNA
<213> ORGANISM: Artificial Sequence
<220> FEATURE:
<223> OTHER INFORMATION: This sequence is synthesized in lab.

<400> SEQUENCE: 2

caggttcagc tggtgcagtc tggagctgag gtgaagaagc ctggggcctc agtgaaggtc     60

tcctgcaagg cttctggtta cacctttacc gactttgaaa tgcactgggt gcgacaggcc    120

cctggacaag ggcttgagtg gatgggagat attgatcctg gaactggtga tactgcctac    180

aatctgaagt tcaagggcag agtcaccatg accacagaca catccacgag cacagcctac    240

atggagctga ggagcctgag gtctgacgac acggccgtgt attactgtgc gttgggggcc    300

tttgtttact ggggccaggg aaccctggtc accgtctcct caggcagtac tagcggtggt    360

ggctccgggg gcggttccgg tgggggcggc agcagcgatg ttgtgatgac tcagtctcca    420

ctctccctgc ccgtcacccc tggagagccg gcctccatct cctgcaggtc tagtcagagt    480

cttgcaaaca gttatgggaa cacctatttg tcttggtacc tgcagaagcc agggcagtct    540

ccacagctcc tgatctatgg gatttccaac agattttctg gggtccctga caggttcagt    600

ggcagtggat caggcacaga ttttacactg aaaatcagca gagtggaggc tgaggacgtt    660

ggggtttatt actgcttaca aggtacacat cagccgtaca cgtttggcca ggggaccaag    720

ctggagatca aa                                                        732


<210> SEQ ID NO 3
<211> LENGTH: 466
<212> TYPE: PRT
<213> ORGANISM: Artificial Sequence
<220> FEATURE:
<223> OTHER INFORMATION: This sequence is synthesized in lab.

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Glu Met His Trp Val Arg Gln Ala Pro Gly Gln Gly Leu Glu Trp Met
        35                  40                  45
```

-continued

```
Gly Asp Ile Asp Pro Gly Thr Gly Asp Thr Ala Tyr Asn Leu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Leu Gly Ala Phe Val Tyr Trp Gly Gln Gly Thr Leu Val Thr Val
            100                 105                 110

Ser Ser Gly Ser Thr Ser Gly Gly Gly Ser Gly Gly Gly Ser Gly Gly
        115                 120                 125

Gly Gly Ser Ser Asp Val Val Met Thr Gln Ser Pro Leu Ser Leu Pro
    130                 135                 140

Val Thr Pro Gly Glu Pro Ala Ser Ile Ser Cys Arg Ser Ser Gln Ser
145                 150                 155                 160

Leu Ala Asn Ser Tyr Gly Asn Thr Tyr Leu Ser Trp Tyr Leu Gln Lys
                165                 170                 175

Pro Gly Gln Ser Pro Gln Leu Leu Ile Tyr Gly Ile Ser Asn Arg Phe
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Glu Asp Val Gly Val Tyr Tyr
    210                 215                 220

Cys Leu Gln Gly Thr His Gln Pro Tyr Thr Phe Gly Gln Gly Thr Lys
225                 230                 235                 240

Leu Glu Ile Lys Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Arg Val Lys Phe Ser Arg Ser Ala Asp Ala Pro Ala Tyr Lys
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
```

465

<210> SEQ ID NO 4
<211> LENGTH: 561
<212> TYPE: PRT
<213> ORGANISM: Artificial Sequence
<220> FEATURE:
<223> OTHER INFORMATION: This sequence is synthesized in lab.

<400> SEQUENCE: 4

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Glu Met His Trp Val Arg Gln Ala Pro Gly Gln Gly Leu Glu Trp Met
        35                  40                  45

Gly Asp Ile Asp Pro Gly Thr Gly Asp Thr Ala Tyr Asn Leu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Leu Gly Ala Phe Val Tyr Trp Gly Gln Gly Thr Leu Val Thr Val
            100                 105                 110

Ser Ser Gly Ser Thr Ser Gly Gly Gly Ser Gly Gly Gly Ser Gly Gly
        115                 120                 125

Gly Gly Ser Ser Asp Val Val Met Thr Gln Ser Pro Leu Ser Leu Pro
    130                 135                 140

Val Thr Pro Gly Glu Pro Ala Ser Ile Ser Cys Arg Ser Ser Gln Ser
145                 150                 155                 160

Leu Ala Asn Ser Tyr Gly Asn Thr Tyr Leu Ser Trp Tyr Leu Gln Lys
                165                 170                 175

Pro Gly Gln Ser Pro Gln Leu Leu Ile Tyr Gly Ile Ser Asn Arg Phe
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Glu Asp Val Gly Val Tyr Tyr
    210                 215                 220

Cys Leu Gln Gly Thr His Gln Pro Tyr Thr Phe Gly Gln Gly Thr Lys
225                 230                 235                 240

Leu Glu Ile Lys Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Lys Lys Arg Ile Lys Pro Ile Val Trp Pro Ser Leu Pro Asp
```

```
        355                 360                 365

His Lys Lys Thr Leu Glu His Leu Cys Lys Lys Pro Arg Lys Asn Leu
    370                 375                 380

Asn Val Ser Phe Asn Pro Glu Ser Phe Leu Asp Cys Gln Ile His Arg
385                 390                 395                 400

Val Asp Asp Ile Gln Ala Arg Asp Glu Val Glu Gly Phe Leu Gln Asp
                405                 410                 415

Thr Phe Pro Gln Gln Leu Glu Glu Ser Glu Lys Gln Arg Leu Leu Gly
            420                 425                 430

Ser Asn Gln Glu Glu Ala Tyr Val Thr Met Ser Ser Phe Tyr Gln Asn
        435                 440                 445

Gln Arg Val Lys Phe Ser Arg Ser Ala Asp Ala Pro Ala Tyr Lys Gln
    450                 455                 460

Gly Gln Asn Gln Leu Tyr Asn Glu Leu Asn Leu Gly Arg Arg Glu Glu
465                 470                 475                 480

Tyr Asp Val Leu Asp Lys Arg Arg Gly Arg Asp Pro Glu Met Gly Gly
                485                 490                 495

Lys Pro Arg Arg Lys Asn Pro Gln Glu Gly Leu Tyr Asn Glu Leu Gln
            500                 505                 510

Lys Asp Lys Met Ala Glu Ala Tyr Ser Glu Ile Gly Met Lys Gly Glu
        515                 520                 525

Arg Arg Arg Gly Lys Gly His Asp Gly Leu Tyr Gln Gly Leu Ser Thr
    530                 535                 540

Ala Thr Lys Asp Thr Tyr Asp Ala Leu His Met Gln Ala Leu Pro Pro
545                 550                 555                 560

Arg


<210> SEQ ID NO 5
<211> LENGTH: 737
<212> TYPE: PRT
<213> ORGANISM: Artificial Sequence
<220> FEATURE:
<223> OTHER INFORMATION: This sequence is synthesized in lab.

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Glu Met His Trp Val Arg Gln Ala Pro Gly Gln Gly Leu Glu Trp Met
        35                  40                  45

Gly Asp Ile Asp Pro Gly Thr Gly Asp Thr Ala Tyr Asn Leu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Leu Gly Ala Phe Val Tyr Trp Gly Gln Gly Thr Leu Val Thr Val
            100                 105                 110

Ser Ser Gly Ser Thr Ser Gly Gly Gly Ser Gly Gly Gly Ser Gly Gly
        115                 120                 125

Gly Gly Ser Ser Asp Val Val Met Thr Gln Ser Pro Leu Ser Leu Pro
    130                 135                 140

Val Thr Pro Gly Glu Pro Ala Ser Ile Ser Cys Arg Ser Ser Gln Ser
145                 150                 155                 160
```

-continued

```
Leu Ala Asn Ser Tyr Gly Asn Thr Tyr Leu Ser Trp Tyr Leu Gln Lys
                165                 170                 175

Pro Gly Gln Ser Pro Gln Leu Leu Ile Tyr Gly Ile Ser Asn Arg Phe
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Glu Asp Val Gly Val Tyr Tyr
    210                 215                 220

Cys Leu Gln Gly Thr His Gln Pro Tyr Thr Phe Gly Gln Gly Thr Lys
225                 230                 235                 240

Leu Glu Ile Lys Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Arg Val Lys Phe Ser Arg Ser Ala Asp Ala Pro Ala Tyr Lys
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg Glu Gly Arg Gly Ser Leu Leu Thr Cys Gly Asp Val Glu Glu
465                 470                 475                 480

Asn Pro Gly Pro Met Thr Asn Lys Cys Leu Leu Gln Ile Ala Leu Leu
                485                 490                 495

Leu Cys Phe Ser Thr Thr Ala Leu Ser Gln Val Gln Leu Gln Gln Ser
            500                 505                 510

Gly Pro Gly Leu Val Lys Pro Ser His Thr Leu Ser Leu Thr Cys Thr
        515                 520                 525

Val Ser Gly Gly Ser Ile Ser Ser Gly Gly Tyr Tyr Trp Ser Trp Thr
    530                 535                 540

Arg Gln His Pro Gly Met Gly Leu Glu Trp Ile Gly Tyr Ile Ser Tyr
545                 550                 555                 560

Ser Gly Ser Ile Tyr Tyr Thr Pro Ser Leu Lys Ser Arg Leu Thr Ile
                565                 570                 575
```

Ser Val Asp Thr Ser Lys Asn Gln Phe Ser Leu Lys Leu Ser Ser Val
580 585 590

Thr Ala Ala Asp Thr Ala Val Tyr Tyr Cys Ala Ser Leu Asp Ser Trp
595 600 605

Gly Ser Asn Arg Asp Tyr Trp Gly Gln Gly Thr Leu Val Thr Val Ser
610 615 620

Ser Gly Gly Gly Gly Ser Glu Ile Val Leu Thr Gln Ser Pro Ala Thr
625 630 635 640

Leu Ser Leu Ser Pro Gly Glu Arg Ala Thr Leu Ser Cys Arg Ala Ser
645 650 655

Gln Ser Val Ser Ser Tyr Leu Ala Trp Tyr Gln Gln Lys Pro Gly Gln
660 665 670

Ala Pro Arg Leu Leu Ile Tyr Asp Ala Ser Asn Arg Ala Thr Gly Ile
675 680 685

Pro Ala Arg Phe Ser Gly Ser Gly Ser Gly Thr Asp Phe Thr Leu Thr
690 695 700

Ile Ser Ser Leu Glu Pro Glu Asp Phe Ala Val Tyr Tyr Cys Gln Gln
705 710 715 720

Arg Ser Asn Trp Pro Leu Thr Phe Gly Gly Gly Thr Lys Val Glu Ile
725 730 735

Lys

<210> SEQ ID NO 6
<211> LENGTH: 832
<212> TYPE: PRT
<213> ORGANISM: Artificial Sequence
<220> FEATURE:
<223> OTHER INFORMATION: This sequence is synthesized in lab.

<400> SEQUENCE: 6

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Phe
20 25 30

Glu Met His Trp Val Arg Gln Ala Pro Gly Gln Gly Leu Glu Trp Met
35 40 45

Gly Asp Ile Asp Pro Gly Thr Gly Asp Thr Ala Tyr Asn Leu Lys Phe
50 55 60

Lys Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Leu Gly Ala Phe Val Tyr Trp Gly Gln Gly Thr Leu Val Thr Val
100 105 110

Ser Ser Gly Ser Thr Ser Gly Gly Gly Ser Gly Gly Gly Ser Gly Gly
115 120 125

Gly Gly Ser Ser Asp Val Val Met Thr Gln Ser Pro Leu Ser Leu Pro
130 135 140

Val Thr Pro Gly Glu Pro Ala Ser Ile Ser Cys Arg Ser Ser Gln Ser
145 150 155 160

Leu Ala Asn Ser Tyr Gly Asn Thr Tyr Leu Ser Trp Tyr Leu Gln Lys
165 170 175

Pro Gly Gln Ser Pro Gln Leu Leu Ile Tyr Gly Ile Ser Asn Arg Phe
180 185 190

Ser Gly Val Pro Asp Arg Phe Ser Gly Ser Gly Ser Gly Thr Asp Phe

```
        195                 200                 205

Thr Leu Lys Ile Ser Arg Val Glu Ala Glu Asp Val Gly Val Tyr Tyr
    210                 215                 220

Cys Leu Gln Gly Thr His Gln Pro Tyr Thr Phe Gly Gln Gly Thr Lys
225                 230                 235                 240

Leu Glu Ile Lys Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Lys Lys Arg Ile Lys Pro Ile Val Trp Pro Ser Leu Pro Asp
        355                 360                 365

His Lys Lys Thr Leu Glu His Leu Cys Lys Lys Pro Arg Lys Asn Leu
    370                 375                 380

Asn Val Ser Phe Asn Pro Glu Ser Phe Leu Asp Cys Gln Ile His Arg
385                 390                 395                 400

Val Asp Asp Ile Gln Ala Arg Asp Glu Val Glu Gly Phe Leu Gln Asp
                405                 410                 415

Thr Phe Pro Gln Gln Leu Glu Glu Ser Glu Lys Gln Arg Leu Leu Gly
            420                 425                 430

Ser Asn Gln Glu Glu Ala Tyr Val Thr Met Ser Ser Phe Tyr Gln Asn
        435                 440                 445

Gln Arg Val Lys Phe Ser Arg Ser Ala Asp Ala Pro Ala Tyr Lys Gln
    450                 455                 460

Gly Gln Asn Gln Leu Tyr Asn Glu Leu Asn Leu Gly Arg Arg Glu Glu
465                 470                 475                 480

Tyr Asp Val Leu Asp Lys Arg Arg Gly Arg Asp Pro Glu Met Gly Gly
                485                 490                 495

Lys Pro Arg Arg Lys Asn Pro Gln Glu Gly Leu Tyr Asn Glu Leu Gln
            500                 505                 510

Lys Asp Lys Met Ala Glu Ala Tyr Ser Glu Ile Gly Met Lys Gly Glu
        515                 520                 525

Arg Arg Arg Gly Lys Gly His Asp Gly Leu Tyr Gln Gly Leu Ser Thr
    530                 535                 540

Ala Thr Lys Asp Thr Tyr Asp Ala Leu His Met Gln Ala Leu Pro Pro
545                 550                 555                 560

Arg Glu Gly Arg Gly Ser Leu Leu Thr Cys Gly Asp Val Glu Glu Asn
                565                 570                 575

Pro Gly Pro Met Thr Asn Lys Cys Leu Leu Gln Ile Ala Leu Leu Leu
            580                 585                 590

Cys Phe Ser Thr Thr Ala Leu Ser Gln Val Gln Leu Gln Gln Ser Gly
        595                 600                 605

Pro Gly Leu Val Lys Pro Ser His Thr Leu Ser Leu Thr Cys Thr Val
    610                 615                 620
```

Ser Gly Gly Ser Ile Ser Ser Gly Gly Tyr Tyr Trp Ser Trp Thr Arg
625 630 635 640

Gln His Pro Gly Met Gly Leu Glu Trp Ile Gly Tyr Ile Ser Tyr Ser
645 650 655

Gly Ser Ile Tyr Tyr Thr Pro Ser Leu Lys Ser Arg Leu Thr Ile Ser
660 665 670

Val Asp Thr Ser Lys Asn Gln Phe Ser Leu Lys Leu Ser Ser Val Thr
675 680 685

Ala Ala Asp Thr Ala Val Tyr Tyr Cys Ala Ser Leu Asp Ser Trp Gly
690 695 700

Ser Asn Arg Asp Tyr Trp Gly Gln Gly Thr Leu Val Thr Val Ser Ser
705 710 715 720

Gly Gly Gly Gly Ser Glu Ile Val Leu Thr Gln Ser Pro Ala Thr Leu
725 730 735

Ser Leu Ser Pro Gly Glu Arg Ala Thr Leu Ser Cys Arg Ala Ser Gln
740 745 750

Ser Val Ser Ser Tyr Leu Ala Trp Tyr Gln Gln Lys Pro Gly Gln Ala
755 760 765

Pro Arg Leu Leu Ile Tyr Asp Ala Ser Asn Arg Ala Thr Gly Ile Pro
770 775 780

Ala Arg Phe Ser Gly Ser Gly Ser Gly Thr Asp Phe Thr Leu Thr Ile
785 790 795 800

Ser Ser Leu Glu Pro Glu Asp Phe Ala Val Tyr Tyr Cys Gln Gln Arg
805 810 815

Ser Asn Trp Pro Leu Thr Phe Gly Gly Gly Thr Lys Val Glu Ile Lys
820 825 830

<210> SEQ ID NO 7
<211> LENGTH: 1398
<212> TYPE: DNA
<213> ORGANISM: Artificial Sequence
<220> FEATURE:
<223> OTHER INFORMATION: This sequence is synthesized in lab.

<400> SEQUENCE: 7
caggttcagc tggtgcagtc tggagctgag gtgaagaagc ctggggcctc agtgaaggtc 60
tcctgcaagg cttctggtta cacctttacc gactttgaaa tgcactgggt gcgacaggcc 120
cctggacaag ggcttgagtg gatgggagat attgatcctg gaactggtga tactgcctac 180
aatctgaagt tcaagggcag agtcaccatg accacagaca catccacgag cacagcctac 240
atggagctga ggagcctgag gtctgacgac acggccgtgt attactgtgc gttgggggcc 300
tttgtttact ggggccaggg aaccctggtc accgtctcct caggcagtac tagcggtggt 360
ggctccgggg gcggttccgg tgggggcggc agcagcgatg ttgtgatgac tcagtctcca 420
ctctccctgc ccgtcacccc tggagagccg gcctccatct cctgcaggtc tagtcagagt 480
cttgcaaaca gttatgggaa cacctatttg tcttggtacc tgcagaagcc agggcagtct 540
ccacagctcc tgatctatgg gatttccaac agattttctg gggtccctga caggttcagt 600
ggcagtggat caggcacaga ttttacactg aaaatcagca gagtggaggc tgaggacgtt 660
ggggtttatt actgcttaca aggtacacat cagccgtaca cgtttggcca ggggaccaag 720
ctggagatca aaaccactac cccagcaccg aggccaccca ccccggctcc taccatcgcc 780
tcccagcctc tgtccctgcg tccggaggca tgtagacccg cagctggtgg ggccgtgcat 840
acccggggtc ttgacttcgc ctgcgatatc tacatttggg cccctctggc tggtacttgc 900

```
ggggtcctgc tgctttcact cgtgatcact ctttactgta ggagtaagag gagcaggctc     960

ctgcacagtg actacatgaa catgactccc cgccgccccg ggcccacccg caagcattac    1020

cagccctatg ccccaccacg cgacttcgca gcctatcgct cccgcgtgaa attcagccgc    1080

agcgcagatg ctccagccta caagcagggg cagaaccagc tctacaacga actcaatctt    1140

ggtcggagag aggagtacga cgtgctggac aagcggagag gacgggaccc agaaatgggc    1200

gggaagccgc gcagaaagaa tccccaagag ggcctgtaca acgagctcca aaaggataag    1260

atggcagaag cctatagcga gattggtatg aaaggggaac gcagaagagg caaaggccac    1320

gacggactgt accagggact cagcaccgcc accaaggaca cctatgacgc tcttcacatg    1380

caggccctgc cgcctcgg                                                  1398
```

<210> SEQ ID NO 8
<211> LENGTH: 1683
<212> TYPE: DNA
<213> ORGANISM: Artificial Sequence
<220> FEATURE:
<223> OTHER INFORMATION: This sequence is synthesized in lab.

<400> SEQUENCE: 8

```
caggttcagc tggtgcagtc tggagctgag gtgaagaagc ctggggcctc agtgaaggtc      60

tcctgcaagg cttctggtta cacctttacc gactttgaaa tgcactgggt gcgacaggcc     120

cctggacaag ggcttgagtg gatgggagat attgatcctg gaactggtga tactgcctac     180

aatctgaagt tcaagggcag agtcaccatg accacagaca catccacgag cacagcctac     240

atggagctga ggagcctgag gtctgacgac acggccgtgt attactgtgc gttgggggcc     300

tttgtttact ggggccaggg aaccctggtc accgtctcct caggcagtac tagcggtggt     360

ggctccgggg gcggttccgg tgggggcggc agcagcgatg ttgtgatgac tcagtctcca     420

ctctccctgc ccgtcacccc tggagagccg gcctccatct cctgcaggtc tagtcagagt     480

cttgcaaaca gttatgggaa cacctatttg tcttggtacc tgcagaagcc agggcagtct     540

ccacagctcc tgatctatgg gatttccaac agattttctg gggtccctga caggttcagt     600

ggcagtggat caggcacaga ttttacactg aaaatcagca gagtggaggc tgaggacgtt     660

ggggtttatt actgcttaca aggtacacat cagccgtaca cgtttggcca ggggaccaag     720

ctggagatca aaaccactac cccagcaccg aggccaccca ccccggctcc taccatcgcc     780

tcccagcctc tgtccctgcg tccggaggca tgtagacccg cagctggtgg ggccgtgcat     840

acccggggtc ttgacttcgc ctgcgatatc tacatttggg cccctctggc tggtacttgc     900

ggggtcctgc tgctttcact cgtgatcact ctttactgta ggagtaagag gagcaggctc     960

ctgcacagtg actacatgaa catgactccc cgccgccccg ggcccacccg caagcattac    1020

cagccctatg ccccaccacg cgacttcgca gcctatcgct ccaaaaaaag gattaagcct    1080

atcgtatggc ccagtctccc cgatcacaag aagactctgg aacacctttg taagaaacca    1140

agaaaaaatt taaatgtgag tttcaatcct gaaagtttcc tggactgcca gattcatagg    1200

gtggatgaca ttcaagctag agatgaagtg gaaggttttc tgcaagatac gtttcctcag    1260

caactagaag aatctgagaa gcagaggctt ctgggatcaa atcaagaaga agcatatgtc    1320

accatgtcca gcttctacca aaaccagcgc gtgaaattca gccgcagcgc agatgctcca    1380

gcctacaagc aggggcagaa ccagctctac aacgaactca atcttggtcg gagagaggag    1440

tacgacgtgc tggacaagcg gagaggacgg gacccagaaa tgggcgggaa gccgcgcaga    1500
```

aagaatcccc aagagggcct gtacaacgag ctccaaaagg ataagatggc agaagcctat 1560
agcgagattg gtatgaaagg ggaacgcaga agaggcaaag gccacgacgg actgtaccag 1620
ggactcagca ccgccaccaa ggacacctat gacgctcttc acatgcaggc cctgccgcct 1680
cgg 1683

<210> SEQ ID NO 9
<211> LENGTH: 2211
<212> TYPE: DNA
<213> ORGANISM: Artificial Sequence
<220> FEATURE:
<223> OTHER INFORMATION: This sequence is synthesized in lab.

<400> SEQUENCE: 9
caggttcagc tggtgcagtc tggagctgag gtgaagaagc ctggggcctc agtgaaggtc 60
tcctgcaagg cttctggtta cacctttacc gactttgaaa tgcactgggt gcgacaggcc 120
cctggacaag ggcttgagtg gatgggagat attgatcctg gaactggtga tactgcctac 180
aatctgaagt tcaagggcag agtcaccatg accacagaca catccacgag cacagcctac 240
atggagctga ggagcctgag gtctgacgac acggccgtgt attactgtgc gttgggggcc 300
tttgtttact ggggccaggg aaccctggtc accgtctcct caggcagtac tagcggtggt 360
ggctccgggg gcggttccgg tgggggcggc agcagcgatg ttgtgatgac tcagtctcca 420
ctctccctgc ccgtcacccc tggagagccg gcctccatct cctgcaggtc tagtcagagt 480
cttgcaaaca gttatgggaa cacctatttg tcttggtacc tgcagaagcc agggcagtct 540
ccacagctcc tgatctatgg gatttccaac agattttctg gggtccctga caggttcagt 600
ggcagtggat caggcacaga ttttacactg aaaatcagca gagtggaggc tgaggacgtt 660
ggggtttatt actgcttaca aggtacacat cagccgtaca cgtttggcca ggggaccaag 720
ctggagatca aaaccactac cccagcaccg aggccaccca ccccggctcc taccatcgcc 780
tcccagcctc tgtccctgcg tccggaggca tgtagacccg cagctggtgg ggccgtgcat 840
acccggggtc ttgacttcgc ctgcgatatc tacatttggg cccctctggc tggtacttgc 900
ggggtcctgc tgctttcact cgtgatcact ctttactgta ggagtaagag gagcaggctc 960
ctgcacagtg actacatgaa catgactccc cgccgccccg ggcccacccg caagcattac 1020
cagccctatg ccccaccacg cgacttcgca gcctatcgct cccgcgtgaa attcagccgc 1080
agcgcagatg ctccagccta caagcagggg cagaaccagc tctacaacga actcaatctt 1140
ggtcggagag aggagtacga cgtgctggac aagcggagag gacgggaccc agaaatgggc 1200
gggaagccgc gcagaaagaa tccccaagag ggcctgtaca acgagctcca aaaggataag 1260
atggcagaag cctatagcga gattggtatg aaaggggaac gcagaagagg caaaggccac 1320
gacggactgt accagggact cagcaccgcc accaaggaca cctatgacgc tcttcacatg 1380
caggccctgc cgcctcggga gggaaggggt tctctcctga cctgcggcga tgtggaggag 1440
aaccccggac ccatgaccaa caagtgtctc ctccaaattg ctctcctgtt gtgcttctcc 1500
actacagctc tttcccaggt gcagctacag cagtcgggcc caggactggt gaagccttca 1560
cacaccctgt ccctcacctg cactgtctct ggtggctcca tcagcagtgg tggttactac 1620
tggagttgga cccgtcagca cccagggatg ggcctggagt ggattggata catctcttac 1680
agtgggagta tctattacac tccgtccctc aagagtcgac ttaccatatc agtggacacg 1740
tctaagaacc agttctccct gaagctgagc tctgtgactg ccgcggacac ggccgtatat 1800
tactgtgcga gtttggattc ctggggatct aaccgtgact actggggcca gggaaccctg 1860
gtcaccgtct cgagtggagg tggtggatcc gaaattgtgt tgacgcagtc tccagccacc 1920
ctgtctttgt ctccagggga aagagccacc ctctcctgca gggccagtca gagtgttagc 1980
agctacttag cctggtacca acagaaacct ggccaggctc ccaggctcct catctatgat 2040
gcatccaaca gggccactgg catcccagcc aggttcagtg gcagtgggtc tgggacagac 2100
ttcactctca ccatcagcag cctagagcct gaagattttg cagtttatta ctgtcagcag 2160
cgtagcaact ggccgctcac tttcggcgga gggaccaagg tggagattaa g 2211

<210> SEQ ID NO 10
<211> LENGTH: 2534
<212> TYPE: DNA
<213> ORGANISM: Artificial Sequence
<220> FEATURE:
<223> OTHER INFORMATION: This sequence is synthesized in lab.

<400> SEQUENCE: 10
caggttcagc tggtgcagtc tggagctgag gtgaagaagc ctggggcctc agtgaaggtc 60
tcctgcaagg cttctggtta cacctttacc gactttgaaa tgcactgggt gcgacaggcc 120
cctggacaag ggcttgagtg gatgggagat attgatcctg gaactggtga tactgcctac 180
aatctgaagt tcaagggcag agtcaccatg accacagaca catccacgag cacagcctac 240
atggagctga ggagcctgag gtctgacgac acggccgtgt attactgtgc gttgggggcc 300
tttgtttact ggggccaggg aaccctggtc accgtctcct caggcagtac tagcggtggt 360
ggctccgggg gcggttccgg tgggggcggc agcagcgatg ttgtgatgac tcagtctcca 420
ctctccctgc ccgtcacccc tggagagccg gcctccatct cctgcaggtc tagtcagagt 480
cttgcaaaca gttatgggaa cacctatttg tcttggtacc tgcagaagcc agggcagtct 540
ccacagctcc tgatctatgg gatttccaac agattttctg gggtccctga caggttcagt 600
ggcagtggat caggcacaga ttttacactg aaaatcagca gagtggaggc tgaggacgtt 660
ggggtttatt actgcttaca aggtacacat cagccgtaca cgtttggcca ggggaccaag 720
ctggagatca aaaccactac cccagcaccg aggccaccca ccccggctcc taccatcgcc 780
tcccagcctc tgtccctgcg tccggaggca tgtagacccg cagctggtgg ggccgtgcat 840
acccggggtc ttgacttcgc ctgcgatatc tacatttggg cccctctggc tggtacttgc 900
ggggtcctgc tgctttcact cgtgatcact ctttactgta ggagtaagag gagcaggctc 960
ctgcacagtg actacatgaa catgactccc cgccgccccg ggcccacccg caagcattac 1020
cagccctatg ccccaccacg cgacttcgca gcctatcgct ccaaaaaaag gattaagcct 1080
atcgtatggc ccagtctccc cgatcacaag aagactctgg aacacctttg taagaaacca 1140
agaaaaaatt taaatgtgag tttcaatcct gaaagtttcc tggactgcca gattcatagg 1200
gtggatgaca ttcaagctag agatgaagtg gaaggttttc tgcaagatac gtttcctcag 1260
caactagaag aatctgagaa gcagaggctt ctgggatcaa atcaagaaga agcatatgtc 1320
accatgtcca gcttctacca aaaccagcgc gtgaaattca gccgcagcgc agatgctcca 1380
gcctacaagc aggggcagaa ccagctctac aacgaactca atcttggtcg gagagaggag 1440
tacgacgtgc tggacaagcg gagaggacgg gacccagaaa tgggcgggaa gccgcgcaga 1500
aagaatcccc aagagggcct gtacaacgag ctccaaaagg ataagatggc agaagcctat 1560
agcgagattg gtatgaaagg ggaacgcaga agaggcaaag gccacgacgg actgtaccag 1620
ggactcagca ccgccaccaa ggacacctat gacgctcttc acatgcaggc cctgccgcct 1680

-continued

```
cgggagggaa ggggttctct cctgacctgc ggcgatgtgg aggagaaccc cggacccatg   1740
accaacaagt gtctcctcca aattgctctc ctgttgtgct tctccactac agctctttcc   1800
caggtgcagc tacagcagtc gggcccagga ctggtgaagc cttcacacac cctgtccctc   1860
acctgcactg tctctggtgg ctccatcagc agtggtggtt actactggag ttggacccgt   1920
cagcacccag ggatgggcct ggagtggatt ggatacatct cttacagtgg gagtatctat   1980
tacactccgt ccctcaagag tcgacttacc atatcagtgg acacgtctaa gaaccagttc   2040
tccctgaagc tgagctctgt gactgccgcg gacacggccg tatattactg tgcgagtttg   2100
gattcctggg gatctaaccg tgactactgg ggccagggaa ccctggtcac cgtctcgagt   2160
ggaggtggtg gatccgaaat tgtgttgacg cagtctccag ccaccctgtc tttgtctcca   2220
ggggaaagag ccaccctctc ctgcagggcc agtcagagtg ttagcagcta cttagcctgg   2280
taccaacaga aacctggcca ggctcccagg ctcctcatct atgatgcatc caacagggcc   2340
actggcatcc cagccaggtt cagtggcagt gggtctggga cagacttcac tctcaccatc   2400
agcagcctag agcctgaaga ttttgcagtt tattactgtc agcagcgtag caactggccg   2460
ctcactttcg gcggagggac caaggtggag attaagcgct cactttcggc ggagggacca   2520
aggtggagat taag                                                     2534
```